United States Patent [19]
Delaney et al.

[11] 3,943,240
[45] Mar. 9, 1976

[54] TOOTHPASTE

[75] Inventors: Thomas James Delaney, Piscataway; William Grant Pierson, Flanders, both of N.J.

[73] Assignee: Colgate-Palmolive Company, New York, N.Y.

[22] Filed: Apr. 30, 1974

[21] Appl. No.: 465,476

Related U.S. Application Data

[63] Continuation-in-part of Ser. No. 389,827, Aug. 20, 1973, abandoned, which is a continuation-in-part of Ser. No. 295,094, Oct. 4, 1972.

[52] U.S. Cl. ................................................ 424/49
[51] Int. Cl.² ........................................ A61K 7/16
[58] Field of Search .......................... 424/49–58

[56] References Cited
UNITED STATES PATENTS

| | | | |
|---|---|---|---|
| 1,082,681 | 12/1913 | Danner | 424/49 |
| 1,112,180 | 9/1914 | Westenfelter | 424/49 |
| 1,716,035 | 6/1929 | Donchi | 424/49 |
| 2,024,146 | 12/1935 | Crowther | 424/49 |
| 2,128,917 | 9/1938 | Crocker | 424/49 |
| 3,003,919 | 10/1961 | Broge | 424/49 |
| 3,551,559 | 12/1970 | Miles | 424/49 |
| 3,670,076 | 6/1972 | Muhler | 424/49 |

*Primary Examiner*—Shep K. Rose
*Attorney, Agent, or Firm*—Steven J. Baron; Murray M. Grill; Herbert S. Sylvester

[57] ABSTRACT

Toothpaste containing sodium bicarbonate as the principal abrasive and a lesser amount of another compatible abrasive. Examples of these are chalk, silica, alumina, zirconium silicate or sodium aluminosilicate, or a mixture thereof, said other abrasive constituting at least about 3 percent of the toothpaste.

9 Claims, No Drawings

TOOTHPASTE

This application is a continuation-in-part of our copending application Ser. No. 389,827, filed on Aug. 20, 1973, now abandoned, which in turn is a continuation in part of copending application Ser. No. 295,094, filed Oct. 4, 1972, whose entire disclosure is incorporated by reference.

Cross reference is made to copending application Ser. Nos. 295,068, filed Oct. 4, 1972; 295,073 filed on Oct. 4, 1972; and 419,741 filed on Nov. 28, 1973, whose entire disclosures are incorporated herein by reference.

This invention relates to toothpastes and more particularly to toothpastes containing dispersed particles of sodium bicarbonate.

Baking soda has been employed in many fields and is a common household ingredient. In past years, its use in dentifrices, particularly tooth powders, has been proposed but has not received much acceptance generally. The typical dentifrices which have significant consumer acceptance in recent years are toothpastes having a high content of water-insoluble abrasives such as dicalcium phosphate or other insoluble phosphates in an aqueous humectant base.

The development of a practical and effective baking soda toothpaste capable of consumer acceptability presents many special considerations. Among the factors which are to be considered are the unique character of baking soda chemically, physically and cosmetically when considered and employed as a toothpaste ingredient. For example, it is comparatively water-insoluble and tends to release carbon dioxide in an aqueous system. It is extremely salty to the taste which is probably one of the more important factors in the purchase and use of a particular product. Other factors in formulation of a suitable product include the over-all cleaning and polishing power of the product, its stability and appearance combined with special care in manufacture, etc.

In accordance with various aspects of this invention, it is now possible to prepare a unique baking soda toothpaste which is effective in promoting hygiene in the oral cavity and capable of consumer desirability or acceptability by the public. Such product will have acceptable cleaning, polishing and other desirable characteristics so as to have a beneficial effect upon parts of the dentition (which may include the teeth and its surrounding or adjacent elements or structures including plaque, calculus, gingiva, mucous membranes, saliva, etc.). In particular, it tends to leave with the consumer a desirable clean mouth or clean mouth-feel effect. The product can be formulated so it is stable upon aging or storage without significant release of carbon dioxide bubbles or other forms of undesirable separation or reaction. It is possible to produce and maintain a unique granular textured appearance comprising a substantially dispersed non-crystalline-appearing granulate which is due in part to the substantially homogeneous distribution of a sufficiently high concentration of macroscopic crystalline bicarbonate particles or granules in an otherwise smooth, continuous base, or matrix, contributing to appearance, taste, effect and usage by the consumer.

One aspect of the invention relates to a toothpaste containing an abrasive content comprising a major proportion of sodium bicarbonate and a minor proportion of a water-insoluble dental abrasive material compatible with said bicarbonate in the dental cream. Thus the toothpaste contains dispersed abrasive particles, the abrasive being a mixture of sodium bicarbonate, which constitutes the major proportion of the abrasive by weight and preferably makes up about 25 to 60 percent of the toothpaste, and a lesser amount of the compatible water-insoluble dental abrasive which may be chalk, silica, alumina, zirconium silicate, sodium aluminosilicate, or other compatible silicate or carbonate which is nonreactive with the bicarbonate, or a mixture of two or more of such water-insoluble abrasives. Advantageously, the amount of water-insoluble abrasive is over 1 percent and preferably at least about 3 percent of the toothpaste, ordinarily about 3–25 percent, more preferably about 5 to 15 percent.

Although the sodium bicarbonate particles are relatively soft as compared to most conventional abrasive particles used in toothpastes they do exert a mechanical cleaning effect on the teeth. For instance, in a radioactive dentin abrasion (RDA) test a toothpaste containing about 50 percent of bicarbonate of soda, as the sole abrasive, may show an RDA value of about 100 whereas when the abrasive-free vehicle of that toothpaste is tested similarly the RDA value is only in the neighborhood of 50.

The toothpastes of this invention preferably contain at least about 20 percent, more preferably at least about 30 percent, sodium bicarbonate. The particle size of the sodium bicarbonate particles may vary; it is preferred that they be largely below 0.4 mm in diameter, with a major proportion by weight having above 0.01 mm in diameter. The vehicle in which the sodium bicarbonate particles are dispersed is preferably aqueous, but its amount and character are preferably such that the sodium bicarbonate is primarily in the undissolved solid state in the toothpaste. It will be understood, however, that when the teeth are brushed the sodium bicarbonate particles will tend to dissolve in the saliva.

In one particularly preferred form of the invention the added abrasive is chalk. It is found that only a small proportion of this ingredient (e.g. in the range of about 5 to 15 percent of the toothpaste) greatly improves the cleaning power of the sodium bicarbonate toothpaste. In addition, the presence of the chalk appears to promote an improvement in the stability of the toothpaste on aging at elevated temperatures such as a decrease in the tendency for essential oils, used as flavors, to separate from the toothpaste on aging at 110° F or 120° F, e.g. when the particles of sodium bicarbonate are of relatively large size, e.g. over 150 microns in diameter.

The addition of the compatible water-insoluble abrasive such as chalk, silica, alumina, zirconium silicate, and the like, or mixtures thereof is found to yield a sodium bicarbonate toothpaste which has improved cleaning power combined with resistance to flavor separation and which does not tend to form gas on storage. In contrast, when such common dental abrasives as dicalcium phosphate or insoluble sodium metaphosphate are added to the sodium bicarbonate toothpaste considerable quantities of gas are formed even on short term storage (e.g. at 120° F).

The average particle size of the chalk is preferably less than 20 microns, most preferably below 10 microns, and above 1 micron.

The silica may be of the crystalline or amorphous type. In either case the particle size is preferably below 20 microns, e.g. 2 to 10 microns. Micronized crystalline silica or silica gel, such as the silica gels sold as Syloid 63, Syloid 74 and Syloid 244 are examples.

The alumina may be of the hydrated or unhydrated type. For hydrated alumina the average particle size is preferably less than 20 microns, most preferably below 10 microns and above 1 or 2 microns.

When zirconium silicate is employed its average particle size is preferably below 5 microns, e.g., below 3 microns and above 0.3 micron.

One particularly suitable alumina is in the form of flat flakes of alpha-alumina crystals, of disk- or plate-like configuration, said flakes having a mean (by weight) particle diameter of less than about 7 microns (e.g. about 2 to 7 microns). The flat alpha-alumina crystals, and a process for preparing them, are described in U.S. Pat. No. 3,121,623. The dentrifrice is preferably substantially free of anhydrous alumina particles having diameters above 15 microns and thicknesses above about 2 microns. While it is most preferred to use alumina flakes whose mean particle diameter is less than five microns (e.g. about 3 to 4 microns) it is within the broader scope of this invention to use alumina flakes of larger diameters but similar thickness, such as alumina flakes, described in the aforesaid U.S. Pat. No. 3,121,623 having average diameters of 9, 12 or 15 or more microns, free of particles over 40 microns in diameter (preferably free of particles over about 20 microns in diameter) and substantially free of particles having thicknesses above about 3 microns. In a preferred form of the invention the alpha-alumina flakes are uncoated and free of adhesion to particles of other materials. It is also within the broader scope of the invention to include other alpha-alumina, or other abrasives of Mohs hardness above 6, in admixture with the alpha-alumina flakes. For instance, one may replace about one half of the alumina flakes by a pulverized alpha-alumina of irregular shape and having a mean particle size of about 3 to 4 microns (with all said irregular particles being less than about 7 microns in their largest dimension); thus, the toothpaste may contain, say, 3 percent of the flakes and 2 percent of said irregular particles.

A typical alkali or alkaline earth metal aluminosilicate is a complex having a refractive index of about 1.45, a moisture content of about 5–20 percent (e.g. 10 percent) an alumina content of up to about 10 percent (e.g. 8 percent) a silica content of at least about 70 percent, a sodium oxide (or other alkali metal or alkaline earth metal oxide, e.g. calcium oxide) content of up to about 10 percent (e.g. 7 percent) and a particle size of below 40 microns, preferably about 1 to 20 microns.

Examples of mixtures are blends of chalk and hydrated alumina, in, say, equal amounts, or about 25/75 or about 75/25.

The toothpaste may also contain a small amount of titanium dioxide powder, which has been found to have a marked polishing effect on the teeth when used in the sodium bicarbonate toothpaste.

The weight of titanium dioxide particles in the toothpaste about 0.1 percent less than about 10 percent the weight of the sodium bicarbonate, preferably about 0.1 to about 5 percent, optimally about 0.5 to about 2.0 percent thereof, but is generally above about 0.1 percent of the weight of the toothpaste. The foregoing can be readily calculated from the ratios of the other respective ingredients, the amount of water present (i.e., 5–35 percent), the water-glycerol ratio (i.e., 3:1 to 6:1), the amount of sodium bicarbonate (i.e. 25–60 percent), the amount of additional abrasive (i.e., 3–25 percent), etc. For instance, the amount of $TiO_2$ may be included to amounts up to about 6.0, preferably about 0.2 to 0.6 percent of the weight of the toothpaste. The particle size of the $TiO_2$ is preferably about 0.1 to 1 micron.

The vehicle of the toothpaste is made up of suitable liquid preferably containing a thickening agent (e.g. a gelling agent). As indicated the vehicle is preferably aqueous, but it is within the broader scope of the invention to employ nonaqueous vehicles. Generally the liquid will contain a humectant or other viscous water-miscible material such as glycerol, sorbitol, polyethylene glycol, mannitol or mixtures thereof. When water is present it preferably constitutes about 5 to 35 percent (e.g. about 10 to 30 percent) of the total vehicle. Superior results (such as better taste) are obtained when the proportion of water is relatively low, e.g. about 10 to 20 percent of the total toothpaste, such as when the sodium bicarbonate:water ratio is in the range of about 3:1 to 6:1.

Gelling agents for toothpaste vehicles are well known in the art. These are often high polymers (e.g. gums or other thickening agents) which are soluble or swellable in water or aqueous medium. Sodium carboxymethylcellulose has given excellent results. Other materials are gum tragacanth, gum arabic, gum karaya, sodium alginate, hydroxyethyl cellulose, methyl cellulose, ethyl cellulose, carrageen and other polysaccharides, polyvinyl pyrollidones or such thickening agents as "Veegum" (a complex magnesium aluminum silicate). The amount of thickening agent used in the practice of this invention is preferably sufficient to impart to the mixture the pasty consistency, body and the non-tacky nature which is characteristic of conventional dental creams or toothpastes. As is well known, such dental creams are extrudable from ordinary collapsible toothpaste tubes to form a ribbon of substantial thickness (e.g. about ⅜ inch) which is left undisturbed, substantially retains its original thickness over a period of, say, one minute or more (and does not penetrate substantially into the bristles of a toothbrush when resting on the ends of such bristles for a similar period); but which preferably offers no substantial resistance to brushing or to deformation when, for instance, one touches it lightly with a finger; and which has little tack, in that it does not tend to form a string when the finger is pulled away from the ribbon. The proportion of thickening agent is often within the range of about 0.5 to 2 percent, such as about 0.8 to 1.5 percent, of the toothpaste.

An organic surface active agent is preferably used in the compositions of the present invention to aid in the prophylactic action and in the thorough dispersion of the composition throughout the oral cavity, and to improve cosmetic acceptability and detersive and foaming properties. Among these are water-soluble salts of the higher alkyl sulfates, such as sodium lauryl sulfate or other suitable alkyl sulfate having 8 to 18 carbon atoms in the alkyl group; water-soluble salts of sulfonated monoglycerides of higher fatty acids such as sodium coconut monoglyceride sulfonate or other suitable sulfonated monoglyceride of a fatty acid of 10 to 18 carbon atoms; salts of amides of higher fatty acid (e.g. 12 to 16 carbon atom acids) with lower aliphatic amino acids (e.g. taurine or sarcosine) or other amino acid of 2 to 6 carbon atoms, such as sodium-N-methyl- N-palmitoyl tauride, sodium N-lauroyl, N-myristoyl or N-palmitoyl sarcosinates; water-soluble salt of the esters of such fatty acids with isethionic acid or with glycerol monosulfate, such as the sodium salt of the monosulfated monoglyceride of hydrogenated coconut oil fatty acids; water-soluble salts of olefin sulfonates, e.g. alkene sulfonates or hydroxyalkane sulfonates or mixtures thereof having 12 to 16 carbon atoms in the carbon chain of the molecule; water-soluble soaps of higher fatty acids such as those of 12-18 carbon atoms e.g. coconut fatty acids. The cation of the salt may be, for instance, sodium (which is preferred) potassium or mono-di- or triethanolamine. Mixtures of surface-active agents may be used. A particularly suitable mixture which provides a high foaming powder with little or no irritating effect comprises a higher alkyl sulfate and a higher fatty acid sarcosinate, e.g. in a ratio of about 1:2 to 2:1, such as about 1:1; instead of all or part of the sarcosinate a higher fatty acid monoglyceride sulfonate may be present.

Other suitable surface-active materials include non-ionic agents such as condensates of sorbitan monostearate with approximately 60 moles of ethylene oxide, condensates of ethylene oxide with propylene oxide condensate of propylene glycol (available under the trademark "Pluronics") and amphoteric agents such as quaternized imidazole derivatives which are available under the trademark "Miranol" such as Miranol $C_2M$. Cationic surface-active germicides and anti-bacterial compounds may also be used. Such compounds include di-isobutylphenoxyethoxyethyl dimethyl benzyl ammonium chloride, benzyl dimethyl stearyl ammonium chloride, tertiary amines, having one fatty alkyl group (or from 12 to 18 carbon atoms) and two (poly) oxyethylene groups attached to the nitrogen (typically containing a total of from about 2 to 50 ethenoxy groups per molecule) and salts thereof with acids, and compounds of the structure:

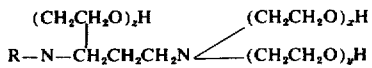

where R is a fatty alkyl group consisting from about 12 to 18 carbon atoms, and $x$, $y$ and $z$ total 3 or higher, as well as salts thereof with mineral or organic acids. It is preferred to use from about 0.05 to 5 percent by weight of the foregoing surface-active materials in the instant dentifrice preparations.

The proportion of surface-active agent is preferably within the range of about 0.05–5 percent of the toothpaste, more preferably in the range of about 1 to 3 percent, such as about 1½ to 2 percent.

In accordance with certain aspects of this invention, cationic antibacterial agents are included in the compositions of the present invention. Such agents include:

$N^1$-(4-chlorobenzyl)-$N^5$-(2,--dichlorobenzyl) biguanide
p-chlorophenyl biguanide
4-chlorobenzyhydryl biguanide;
4-chlorobenzhydrylguanylurea;
N-3-lauroxpropyl-$N^5$-p-chlorobenzylbiguanide;
1-(lauryldimethylammonium)-8-/p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis (2-ethylhexyl)-5-methylhexahydropyrimidine cetyl pyridinium chloride and their non-toxic acid addition salts, particularly the fluorides and the dihydrogen fluorides. 1,6-di-(p-chlorophenylbiguanidohexane) is particularly preferred. These agents may be used in amounts ranging from about 0.01 to 5 percent by weight of the dentifrice.

Any suitable flavoring or sweetening materials may be employed in formulating a flavor for the compositions of the present invention. Examples of suitable flavoring consitutents include the flavoring oils, for example, oils of spearmint, peppermint, wintergreen, sassafras, clove, sage, eucalyptus, marjoram, cinnamon, lemon and orange, as well as sodium methylsalicylate. Suitable sweetening agents include lactose, maltose, sorbitol, sodium cyclamate, perillartine, saccharine and ammoninated glycyrrhizin (e.g. its monoammonium salt). Suitably, flavor and sweetening agent together comprise from about 0.01 to 5 percent or more of the compositions of the instant invention. Preferably the amount of flavoring oil is above 0.5 percent, e.g. 0.8 to 1.2 percent.

The dental cream may also contain a fluoride-containing-anticaries agent. There are many water-soluble inorganic salts which are suitable sources of fluoride ions. Among these are sodium, potassium, ammonium, and lithium and amine fluorides. The monofluorophosphate salts are also useful and include $Na_4P_3O_9F$, $K_4P_3O_9F$, $(NH_4)_4P_3O_9F$, $Na_3KP_3O_9E$, $1)_3 NaP_3O_9F$, and $Li_4P_3O_9F$. Complex water-soluble fluoride-containing salts such as fluorosilicate (i.e., $Na_2SiF_6$), fluorozirconate (i.e., $Na_2ZrF_6$), fluorostannite (i.e., $KSnF_3$), fluoroborate (i.e., $NaBF_4$), fluorotitanate (i.e., $NaTiF_5$), and fluorogermanate (i.e., $K_2GeF_6$) may also be useful. The fluoride ion may also be supplied by an organic fluoride which yields fluoride ions in water. Suitable organic compounds include mono-, di-, and triethanolamine hydrofluoride. These materials are present in an effective but non-toxic amount, usually within the range to provide about 0.01 to 1 percent by weight of the water-soluble fluorine content thereof to the dentifrice. Sodium fluoride, and sodium monofluorophosphate are the preferred compounds.

Various other materials may be incorporated into the dentifrice preparations of this invention. Examples thereof are coloring and whitening agents, preservatives, silicones, chlorophyll compounds, and mixtures thereof, and other constituents. These adjuvants are incorporated in the instant compositions in amounts which do not substantially adversely affect the properties and characteristics desired and are selected and used in proper amount depending upon the particular type of preparation involved.

The following Examples are given to illustrate this invention further. In this application all proportions are by weight unless otherwise indicated.

EXAMPLE 1

A toothpaste is prepared by forming a gel by mixing a gelling agent, in this case sodium carboxymethylcellulose ("CMC"), with glycerol and water (in the presence of a sweetener, sodium saccharin, and a preservative, sodium benzoate), adding sodium bicarbonate (baking soda) chalk and titanium dioxide powder to the gel, then adding a surfactant, a flavor and thereafter degassing the mixture under vacuum. The proportions used are: baking soda, 35%; chalk, 10%; titanium dioxide, 0.4%; deionized water, 15.4%; glycerol, 33.5%; CMC, 1.1%; solution of 35% sodium N-lauroyl sarcosinate in a mixture of 35% water and 30% glycerol, 2%; sodium lauryl sulfate, 0.98%; sodium benzoate, 0.5%; sodium saccharin, 0.2%; flavor, 0.9%.

The baking soda powder is U.S.P. grade having the following particle size distribution in which percentages represent the cumulative percent retained on the named sieve, and sieve sizes are U.S. Standard; No. 45 sieve, trace; No. 70 sieve (sieve opening 210 microns), 27 percent; No. 80 sieve (sieve opening 177 microns) 66.5 percent; No. 100 sieve (sieve opening 149 microns), 92.5 percent; No. 170 sieve (sieve opening 88 microns), 99%.

The chalk is a grit-free U.S.P. Non Fer Al Chalk containing at least 98% $CaCO_3$ with no more than 0.2 percent insoluble in dilute HCl. Its particle size is such that over 99 percent passes through a U.S. Standard No. 325 mesh sieve, the particles being principally in the 1 to 10 micron size, the average particle size being about 3 microns.

The titanium dioxide used is a grit-free anatase powder at least 99.0 percent of which passes through a No. 325 U.S. Standard sieve and whose mean particle diameter (as measured on a Mahn sedimentation balance) is below 1 micron. Microscopic measurements indicate its average particle diameter is 0.3 micron.

The toothpaste has good cleaning power and whiteness and ages well in tests at 8° F, 40° F, 110° F, 120° F. Because of the relatively large particle size of the baking soda a ribbon of the toothpaste, extruded from its tube, has a finely textured grainy appearance to the naked eye. The toothpaste has a pleasant feel during brushing; while the large particles of baking soda are palpable they break down to smaller particles easily under the pressure of the toothbrush and under the action of the saliva.

EXAMPLE 2

Example 1 is repeated except that 5% hydrated alumina is substituted for the 10% chalk, the proportion of baking soda is correspondingly increased to 40 percent and the flavor used is a blend of essential oils, largely peppermint.

The hydrated alumina has the following particle size distribution, and is alpha alumina trihydrate:

28–40 percent finer than 5 microns
56–67 percent finer than 10 microns
85–93 percent finer than 20 microns
94–99 percent finer than 30 microns

EXAMPLE 3

Example 2 is repeated except that instead of the 5% of hydrated alumina there is employed 5% zirconium silicate powder of the following particle size distribution:

80% finer than 1.25 microns
90% finer than 1.77 microns
95% finer than 2.15 microns
99% finer than 2.50 microns

EXAMPLE 4

Example 2 is repeated except that instead of the 5% of hydrated alumina there is used 5% of micronized silica, and half the baking soda is replaced by a more finely divided baking soda having the following particle size distribution (in which percentages represent the cumulative per cent retained on the named sieve, and sieve sizes are U.S. Standard): No. 45 seive (seive opening 350 microns), trace; No. 100 sieve (sieve opening 149 microns), 0.5 percent; No. 170 sieve (sieve opening 88 microns), 20 percent; No. 200 sieve (sieve opening 74 microns), 35 percent; No. 325 sieve (sieve opening 44 microns), 70 percent; No. 400 sieve, 80%.

It is also within the broader scope of the invention to use calcium pyrophosphate (e.g. the $\beta$ or $\gamma$ form of calcium pyrophosphate, or mixtures of those forms in various proportions such as in about 1:1 ratio, e.g. 53% $\beta$, 47% $\gamma$), having an average particle size below about 20 microns, e.g. about 1 or 2 to 10 microns, for all or part of the water-insoluble abrasive in the toothpaste.

Another aspect of this invention relates to the degassing of toothpastes containing high proportions of sodium bicarbonate particles. It is found that when such toothpastes are subjected to high vacuum, e.g. above 26 inches of mercury, the paste bubbles and expands but, unlike conventional toothpastes, it does not contract to substantially its original volume on continuted vacuum treatment, but instead continues to expand. It has now been found that an excellent deaerated product, having good stability and desirable rheological characteristics can be produced by subjecting the toothpaste containing sodium bicarbonate to a vacuum of at least 26 inches of mercury so that it expands to a volume which is at least 150 percent (e.g. about 200 percent) of its volume at atmospheric pressure and then discontinuing the treatment at high vacuum when the expanded mixture begins to contract but while its volume is still at least 150 percent of its volume at atmospheric pressure.

EXAMPLE 5

This Example illustrates the degassing treatment of this invention.

18.3 parts of glycerol; 1.1 part of sodium carboxymethyl cellulose; 0.5 part of sodium benzoate; 0.2 part of sodium saccharin and 15.4 parts of water are mixed at 110°–115° F. for 20 minutes and placed in a vertical cylindrical container equipped with a stirrer, specifically a Dopp mixer which has a series of intermeshing counter-rotating radially disposed mixing rods located all along its height. Then five parts of calcium carbonate (chalk), 40 parts of sodium bicarbonate, 0.4 part of titanium dioxide are added and mixed slowly while a vacuum of 27½ inches of mercury is applied; the speed of mixing is then increased; during this vacuum treatment, which lasts about 5 minutes, the batch rises to a volume about two-thirds greater than its volume before vacuum is applied and then decreases somewhat. The mixture is then vented to the atmosphere and 0.975 parts of sodium lauryl sulfate and 2 parts of a solution of 35 percent sodium lauroyl sarcosinate in a water-glycerol (35–30 percent) mixture are then added, a vacuum 28.2 inches of mercury is applied and the mixture is kept under the vacuum for about 5 minutes while stirring; during this time, the volume of the batch increases and decreases somewhat, the volumes being little greater than observed during the preceding vacuum treatment. The mixture is then vented to the atmosphere. 15.1 parts of glycerol are added and the mixture is then stirred under a vacuum of 28 inches of mercury for about 5 minutes during which treatment its volume increases by more than 100 percent (i.e. to a volume which is more than 200 percent of the original volume) and then begins to decrease somewhat. At the conclusion of this 5 minute period, the vessel is vented to the atmosphere while the volume of the mixture is still about 75–100 percent greater than its volume just prior to this vacuum treatment. One part of essential oil flavor is then added, stirring is resumed while a vacuum of 28½ inches is applied; stirring under this vacuum is continued for about 12 minutes, after which the vessel is vented to the atmosphere; during this 12 minute period, the expansion of the mixture is similar to that observed during the immediately preceding vacuum treatment. Just before the mixture is vented to the atmosphere, the expansion of the mixture is still in progress.

It is preferable to discontinue the vacuum treatment, despite continued formation of gas bubbles, before the change in pH (i.e. the pH of the vacuum treated mixture minus the pH of the mixture without vacuum treatment) reaches one pH unit and preferably less, e.g. ½ unit; this avoids decomposition of sodium bicarbonate and production of sodium carbonate during degassing.

EXAMPLE 6

This Example illustrates the use of alpha alumina flakes in the baking soda toothpaste.

The toothpaste is made up (using, for instance, the method of Example 1) of 40 percent of the baking soda powder of Example 1, 5 percent of alpha-alumina flakes, 0.4 percent titanium dioxide of Example 1, 33.4 percent glycerol, 15.4 percent deionized water, 1.1 percent CMC (Hercules 7MF), 2 percent of a solution of 35 percent sodium N-lauroyl sarcosinate in a mixture of 35 percent water and 30 percent glycerol, 1 percent sodium lauryl sulfate, 1 percent flavor (water-insoluble essential oil flavoring agent; e.g., essential oil mixture rich in peppermint oil), 0.5 percent sodium benzoate and 0.2 percent sodium sachharin.

The alpha alumina flakes have a mean (by weight) particle diameter of about 4 microns, all the particles thereof have diameters less than 10.1 microns, about 85–95 percent (by weight) have diameters less than 6.0 microns and about 30–35 percent have particle diameters less than 3.5 microns.

The characteristics of the toothpaste of this Example are like those given in Example 1 above. It has very good resistance to flavor separation. It also shows much greater polishing effect on the enamel, than the toothpaste of Example 1.

EXAMPLE 7

Example 6 is repeated except that the toothpaste contains 0.22 percent sodium fluoride (the glycerine content being correspondingly decreased by 0.22 percent). The toothpaste shows excellent aging characteristics including very good resistance to flavor separation on aging and very good retention of fluoride content. Like the toothpaste of Example 7, it has a high polishing effect on enamel; its percent repolish is 64 percent.

The percent repolish is determined by a test in which sections of human dental enamel, upon which have been ground flat areas, are first polished, then dulled with chalk, and then brushed with a slurry of a dentifrice for 5000 reciprocal strokes. A "Monsanto Tooth Reflectance Instrument" is employed to measure the specular reflectance of the surface after each step described above. The dulled surface is adjusted so that it is approximately 150 units (Monsanto Instrument) lower than the polished surface. The polishing ability of the dentifrice is expressed by the following equation:

$$\text{Percent Repolish} = \frac{(SR\ 5000\ \text{strokes} - SR\ \text{dulled})100}{SR\ \text{polished} - SR\ \text{dulled}}$$

Where SR polished, SR dulled and SR 5000 strokes are respectively the specular reflectance values of the enamel surface after the initial polishing, after dulling with chalk, and after brushing with a dentifrice slurry.

EXAMPLE 8

Example 6 is repeated except that the toothpaste contains 0.76 percent sodium monofluorophosphate (the glycerine content being correspondingly decreased by 0.76 percent).

EXAMPLE 9

Examples 6, 7 and 8 are repeated except that the alpha-alumina flakes have a mean particle diameter of 5 microns, substantially all being less than about 12 microns in diameter.

EXAMPLE 10

This Example illustrates the use of unlined aluminum toothpaste tubes with certain baking soda toothpastes.

(a) A toothpaste is made up (using, for instance, the method of Example 1) of 40 percent of the baking soda powder (of Example 1) 5 percent of calcium carbonate, (of Example 1), 0.4 percent titanium dioxide of Example 1, 33.4 percent glycerol, 15.4 percent deionized water, 1.1 percent CMC (Hercules 7MF), 2 percent of a solution of 35 percent sodium N-lauroyl sarcosinate in a mixture of 35 percent water and 30 percent glycerol, about 1 percent sodium lauryl sulfate, 1 flavor (water-insoluble essential oil flavoring agent; e.g., essential oil mixture rich in peppermint oil), 0.5 percent sodium benzoate, and 0.2 percent sodium saccharin.

(b) Example 10a is repeated except that 0.5 percent of fumed silica (Cab-O-Sil) is included, the amount of calcium carbonate is raised to 10 percent, the amount of baking soda is decreased to 35 percent and amount of glycerol is decreased to 32.9 percent.

(c) Example 10b is repeated except that the amount of calcium carbonate is decreased to 5 percent and the amount of glycerol is raised to 37.9 percent.

(d) Example 10a is repeated four times, with additional inclusion of various proportions of non-acidic dicalcium phosphate dihydrate in the formuation, i.e., in amounts of 0.04, 0.2, 0.4 and 0.8 percent (based on the weight of the formulation without said phosphate); the first case (0.04 percent) the titanium dioxide is omitted. The dicalcium phosphate dihydrate is of dentifrice grade and has an average particle diameter of about 4 microns and its pH (measured in 20 percent slurry thereof in water) is in the range of 7.2 to 7.9; it yields phosphate ions on contact with water.

(e) Example 10a is repeated with the additional inclusion of insoluble sodium metaphosphate in the formulation in the amount of 0.8 percent (based on the weight of the formulation without said phosphate). The insoluble sodium metaphosphate is of dentifrice grade having an average particle size of about 5 microns; its pH (measured in 20 percent slurry thereof in water) is in the range of 5.3 to 6.3; it yields phosphate ions on contact with water.

(f) Example 10a is repeated except that 5 percent micronized silica is substituted for the calcium carbonate, a different essential oil flavor is used, the amount of flavor is 0.9 percent and the amount of glycerol is 33.5 percent.

(g) Example 10a is repeated except that 3 percent micronized silica is included, the calcium carbonate is omitted, the amount of baking soda is increased to 42 percent and the toothpaste contains 0.9 percent of an essential oil flavor.

(h) Example 10a is repeated except that 5 percent precipitated silica is substituted for the calcium carbonate;

(i) Example 10a is repeated except that 5 percent anhydrous dicalcium phosphate is substituted for the calcium carbonate, the toothpaste contains 0.9 percent of an essential oil flavor and the amount of glycerol is increased to 33.5 percent). The anhydrous dicalcium phosphate is a fine non-acidic powder of dentifrice grade. Its pH (as measured on a 20 percent slurry thereof in water) is 7.6–7.8; it yields phosphate ions, in low concentration, on contact with water.

(j) Example 10a is repeated except that 5 percent zirconium silicate of Example 3 is substituted for the calcium carbonate (with minor change in proportion and type of flavor).

(k) Example 10a is repeated except that 5 percent beta phase calcium pyrophosphate is substituted for the calcium carbonate. The calcium pyrophosphate is a fine powder of dentifrice grade. Its pH (as measured on a 20 percent slurry thereof in water) is 5.2–5.3.

Each of the foregoing toothpastes is placed in an individual toothpaste tube of unlined aluminum of high purity (99.7 percent Al or purer) and aged. On aging at 120° F the tube filled with the 10a toothpaste tends to swell or is found to have a foamy product film in contact with the inner aluminum walls of the tube, tubes filed with the 10b, c, d, f, g, h, i, j, and k toothpastes do not show such effects. The 10e toothpaste shows substantially less tendency to react with the walls of the tube then the 10a toothpaste.

The fumed silica (as in Example 10b) is described in Encyclopedia of Chemical Technology Kirk-Othmer 2nd Edition, Vol. 18 at pages 62 and 67, for instance. It is within the broader scope of the invention to use the fumed silica in baking soda toothpaste from which the compatible water-insoluble abrasive (such as calcium carboante) has been omitted, in unlined aluminum tubes. It is also within the broader scope of the invention to employ, in place of the fumed silica, very finely dispersed or dissolved silica in other forms such as alkali metal silica such as sodium silicate, e.g. hydrated sodium silicate supplied in flake form containing $Na_2O \cdot SiO_2 \cdot H_2O$ in a ratio of about 1:2–3.2:5, or sodium silicate solutions (water glass) such as those in which the $Na_2O:SiO_2$ ratio is at least about 1:2, or sodium silicate formed in situ in the dental cream, or colloidal silica or precipitated silica (see Encyclopedia of Chemical Technology, Kirk-Othmer, 2nd edition Vol. 18, pages 63 and 66–67, for instance) or other silicate.

The decalcium phosphate dihydrate of Example 10d is a commercial stabilized dentifrice grade of this material. A description of the method of preparation of dicalcium phosphate dihydrate and of its stabilization is found in U.S. patent of Schlaeger et al. U.S. Pat. No. 3,169,096 Feb. 9, 1965, whose disclosure is incorporated herein by reference. See also "Cosmetic Science" Vol. 1 pub. 1972 (Wiley Interscience) edited by Balsam and Sagarin pages 477–479. One typical analysis of dicalcium phosphate dihydrate indicates that its content of water-soluble material is 0.18 percent (and its percent water-solubles expressed as $P_2O_5$ is 0.11 percent). A typical stabilizer content is a mixture of about 1–2 percent of sodium calcium pyrophosphate and a smaller amount, e.g. about 0.4 percent, of pyrophosphoric acid.

The insoluble sodium metaphosphate of Example 10e is a commercial dentifrice grade of this material. Its method of preparation and properties are described in the previously cited "Cosmetic Science" at pages 480–481 and "Phosphorus and Its Compounds" by Van Wazer Vol. 2 pub. 1961 (Interscience) pages 1652–1653.

The anhydrous dicalcium phosphate of Example 10i and the calcium pyrophosphate of Example 10k are commercial dentifrice grades of these materials. See the previously cited "Phosphorus and Its Compounds" page 1651 and "Cosmetic Science" pages 479–480.

EXAMPLE 11

Example 10a is repeated except that the toothpaste contains added anhydrous disodium phosphate (incorporated as a water-soluble powder) in amount of (a) 0.05 percent and (b) 0.01 percent the amount of water in the toothpaste being adjusted accordingly to total 100 percent. In each case, on aging in unlined aluminum tubes (as in Example 10) the filled tubes do not swell or gas and (after 9 weeks aging at 120° F.) the inner walls of the tubes are found to be gold-colored, the wall color in the tube containing the 11b toothpaste being very light. On inspection of the inner walls of the unlined aluminum tubes containing the 10d toothpastes (again after 9 weeks at 120° F.) they are found to be dark (when the pastes contain 0.8 percent or 0.4 percent of the dicalcium phosphate dihydrate) or golden (when the tubes contain 0.04 and 0.2 percent of the dicalcium phosphate dihydrate); on inspection of the inner walls of the unlined aluminum tubes containing the 10k toothpaste they are found to be golden after 3 and 6 weeks aging at 120° F. and dark after 9 weeks of such aging. It is believed that the toothpastes containing the dicalcium phosphate dihydrate contain (or form, on aging) small amounts of dissolved phosphate ions (e.g. orthophosphate and/or pyrophosphate) which may act on the aluminum walls, or on the aluminum oxide layer on said walls, to form a protective layer thereon. The amount of dissolved phosphate ion present in the preferred compositions is sufficient to inhibit the gas-forming reaction between the alkaline toothpaste composition and the aluminum walls of the tube but the amount of the phosphate or acidic ingredient therein is insufficient to cause a gas-forming reaction (e.g. resulting in swelling or bursting of the tube) between the ingredients of the toothpaste; the tendency for the latter reaction can, of course, be tested by placing the composition in a suitably lined aluminum tube (whose walls are thus substantially inert to the composition) and aging for several weeks (e.g. 9 weeks) at an elevated temperature (e.g. 120° F.).

Storage of the toothpastes of other types in unlined aluminum tubes is discussed in such patents as U.S. Pat. Nos. 3,662,060 and 3,678,155 and Austrian Pat. No. 267,070. As is well known to consumers of toothpastes, aluminum toothpaste tubes are squeezable and deformable to express the toothpaste from the nozzle of the tube and the main body of the tube is of relatively thin, ductile, aluminum.

The baking soda used in the Examples is a product made by precipitation from solution (as by treating a sodium carbonate solution with carbon dioxide to precipitate the bicarbonate) followed by drying, curing with carbon dioxide gas and screening to the desired particle size (generally without substantial crushing or pulverizing).

These particles are generally monoclinic crystals or tablets or conglomerates thereof (e.g. twinned crystals) some having projecting spike-like portions of generally rhombohedral shape with many reentraut angles.

The toothpastes of the foregoing Examples are non-effervescent. Thus when diluted with water they do not actively evolve bubbles of carbon dioxide.

The toothpastes of this invention have an alkaline pH, generally in the range of about 8.5 to 9.5, usually below about 9.1.

The dentin abrasion of the toothpastes may be determined by the procedure based on a ratioactive technique described by Grabenstetts et al. in the "Journal of Dental Research," Volume 37, P. 1060 (1958) as modified by the description by Stookey et al. in the "Journal of Dental Research," Volume 47, page 524 (July–August 1968).

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A dental cream containing an abrasive content comprising at least about 20 percent sodium bicarbonate in a vehicle containing sufficient liquids, said vehicle consisting essentially of about 5 to 35 percent water and sufficient viscous water miscible polyol humectant or mixtures thereof, and a sufficient amount of gelling or thickening agent to impart to the dental cream the pasty consistency, body and non-tacky nature which is characteristic of conventional dental creams or toothpastes, and over 1 percent of a water insoluble dental abrasive material compatible with said bicarbonate in the dental cream, said sodium bicarbonate being primarily in the undissolved solid state, said dental cream having a granular textured appearance comprising a substantially dispersed non-crystalline appearing granulate of macroscopic crystalline bicarbonate granules in an otherwise continuous matrix.

2. A dental cream as in claim 1 wherein said insoluble abrasive is present in amount of at least about 3 percent of the dental cream and is selected from the group consisting of silica, alumina, silicates and carbonates non-reactive with the bicarbonate.

3. A dental cream as in claim 2 wherein the total abrasive content is about 25 – 60 percent and is dispersed in an aqueous humectant medium.

4. A dental cream as in claim 3 which contains calcium carbonate.

5. A dental cream as in claim 3 which contains flat flakes of alpha-alumina.

6. A dental cream as in claim 1 wherein said water insoluble dental abrasive material is included in amounts of about 3–25 percent.

7. A dental cream as in claim 1 wherein the sodium bicarbonate - water ratio is about 3:1 to 6:1.

8. A dental cream as defined in claim 1 further including a non-soap synthetic detergent.

9. A dental cream as defined in claim 1 further including at least about 0–5 percent of a suitable flavoring oil.

* * * * *

UNITED STATES PATENT OFFICE
CERTIFICATE OF CORRECTION

PATENT NO. : 3,943,240
DATED : March 9, 1976
INVENTOR(S) : Thomas James Delaney, et al It is certified that error appears in the above–identified patent and that said Letters Patent are hereby corrected as shown below:

The term of this patent subsequent to January 27, 1993, has been disclaimed.

Signed and Sealed this

Third Day of August 1976

[SEAL]

Attest:

RUTH C. MASON
*Attesting Officer*

C. MARSHALL DANN
*Commissioner of Patents and Trademarks*